United States Patent
Kroll et al.

(10) Patent No.: US 7,076,301 B1
(45) Date of Patent: Jul. 11, 2006

(54) IMPLANTABLE CARDIAC STIMULATION DEVICE THAT MINIMIZES PARASITIC MUSCLE STIMULATION AND METHOD

(75) Inventors: Mark W. Kroll, Simi Valley, CA (US); John W. Poore, South Pasadena, CA (US)

(73) Assignee: Pacesetter, Sylmar, CA (US)

(*) Notice: Subject to any disclaimer, the term of this patent is extended or adjusted under 35 U.S.C. 154(b) by 580 days.

(21) Appl. No.: 10/326,746

(22) Filed: Dec. 20, 2002

(51) Int. Cl.
*A61N 1/362* (2006.01)
*A61N 1/365* (2006.01)

(52) U.S. Cl. .......................................... 607/17; 607/9
(58) Field of Classification Search ............ 607/9, 607/17, 19, 27–28
See application file for complete search history.

(56) References Cited

U.S. PATENT DOCUMENTS

| | | | |
|---|---|---|---|
| 4,905,697 A * | 3/1990 | Heggs et al. .................. 607/18 |
| 5,172,690 A * | 12/1992 | Nappholz et al. ............. 607/13 |
| 5,466,254 A | 11/1995 | Helland ....................... 607/123 |
| 5,669,392 A * | 9/1997 | Ljungstrom .................. 600/510 |
| 5,876,353 A * | 3/1999 | Riff ............................. 600/547 |
| 5,925,067 A | 7/1999 | Lu .............................. 607/28 |
| 6,070,102 A * | 5/2000 | Hartlaub et al. .............. 607/31 |
| 6,615,082 B1 * | 9/2003 | Mandell ....................... 607/11 |
| 2002/0095190 A1 * | 7/2002 | Bornzin et al. .............. 607/28 |

* cited by examiner

*Primary Examiner*—Carl Layno

(57) ABSTRACT

An implantable cardiac stimulation device provides capture of a chamber of a heart with pacing pulses while minimizing parasitic muscle tissue stimulation. A parasitic muscle stimulation detector detects if the application of pacing pulses result in parasitic muscle stimulation. If there is parasitic muscle stimulation resulting from the application of pacing pulses, a pulse generator control adjusts the pacing pulse amplitudes and durations until the pacing pulses capture the chamber of the heart without causing parasitic muscle stimulation.

16 Claims, 6 Drawing Sheets

IMPLANTABLE CARDIAC STIMULATION DEVICE THAT MINIMIZES PARASITIC MUSCLE STIMULATION AND METHOD

FIELD OF THE INVENTION

The present invention generally relates to an implantable cardiac stimulation device that provides pacing therapy to a patient's heart. The present invention more particularly relates to such a device that minimizes parasitic muscle tissue stimulation while capturing the heart notwithstanding high capture thresholds.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as comprising two major components. One component is a pulse generator which generates the pacing stimulation pulses and includes the electronic circuitry and the power cell or battery. The other component is the lead, or leads, having electrodes which electrically couple the pulse generator to the heart. A lead may provide both unipolar and bipolar pacing polarity electrode configurations. In unipolar pacing, the pacing stimulation pulses are applied between a single electrode carried by the lead, in electrical contact with the desired heart chamber, and the pulse generator case. The electrode serves as the cathode (negative pole) and the case serves as the anode (positive pole). In bipolar pacing, the pacing stimulation pulses are applied between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Traditionally, therapy delivery had been limited to the venous, or right side of the heart. The reason for this is that implanted electrodes can cause blood clot formation in some patients. If a blood clot were released arterially from the left heart, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, or cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation.

While left heart side pacing represents a significant advancement for those patients which require such therapy, it itself is not without its own challenges. One such challenge relates to capture threshold. More specifically, it has been found that the capture thresholds, which must be exceeded to effectively pace the heart, are generally higher for left heart side pacing then for right heart side pacing. Interestingly, the potential complication is not in the ability of a device to have sufficient output to capture the particular heart chamber, but the possibility of stimulating muscle tissue other than the desired heart muscle in the process.

The other muscle tissue mentioned above will be referred to herein as parasitic muscle tissue which includes any muscle tissue other than the muscle tissue of the particular heart chamber to be captured by the pacing pulses. Typically the parasitic muscle tissue stimulation would be chest muscle, but other non-cardiac muscle tissue may also be involved.

It is now common for pacemakers to have automatic capture determination functionality for automatically setting the pacing pulse output amplitude (current or voltage) to a level required to exceed a heart chamber pacing threshold to capture and thus effectively pace the heart chamber. Typically, the determination is made over a range of output levels at a constant pulse duration until the capture threshold is found. The device output is then set to the threshold plus an added safety margin. A constant pulse duration is used because the capture threshold voltage or current varies with pulse duration.

The stimulation threshold of parasitic muscle tissue generally does not vary with pulse duration and is substantially constant. For capture thresholds in a normal range, the output amplitude to which the device is automatically set essentially never exceeds the stimulation threshold of parasitic muscle tissue. However, for higher capture thresholds, and especially those of left heart side pacing, the automatically set device output can not only exceed the pacing capture threshold, but the parasitic muscle tissue stimulation threshold as well. As a result, the present invention addresses this issue.

SUMMARY

In one embodiment, an implantable cardiac stimulation device is disclosed that comprises a pulse generator adapted to provide pacing pulses to a chamber of a heart of a patient. The device further comprises a pulse generator control circuit that adjusts parameters of the pacing pulses to enable the pacing pulses to capture the chamber of the heart while minimizing stimulation of parasitic muscle tissue of the patient.

The device may further include a parasitic muscle tissue stimulation detector. The detector detects stimulation of parasitic muscle tissue in response to a pacing pulse. The control circuit may then adjust parameters of the pacing pulses when the parasitic muscle tissue detector detects parasitic muscle tissue stimulation.

In another embodiment, a cardiac stimulation device comprises a pulse generator that applies stimulation pulses to a chamber of a heart of a patient, a physiologic sensor that senses muscle activity of the patient and that provides an activity signal, and a parasitic muscle tissue stimulation detector that processes the activity signal and detects parasitic muscle tissue stimulation resulting from the stimulation pulses.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
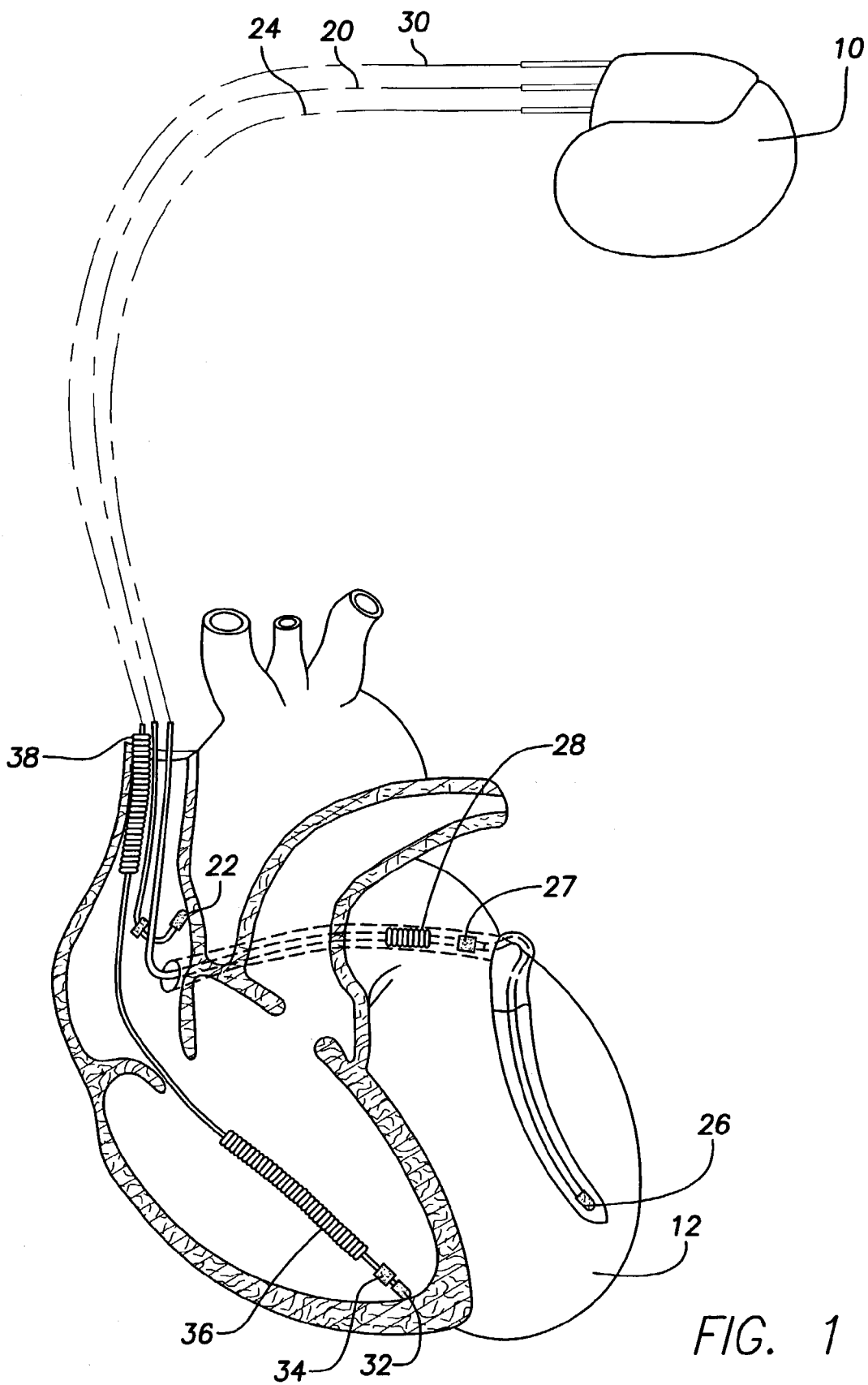
FIG. 1 is a simplified diagram illustrating an implantable stimulation device embodying the present invention capable of delivering multi-chamber stimulation and shock therapy.

As shown in FIG. 1, there is a stimulation device 10 including a lead system of three leads, 20, 24 and 30, for delivering multi-chamber stimulation and shock therapy. To sense atrial cardiac signals and to provide right atrial chamber stimulation therapy, the stimulation device 10 includes an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 includes a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28. For a complete description of a coronary sinus lead, U.S. Pat. No. 5,466,254, "Coronary Sinus Lead with Atrial Sensing Capability" (Helland), which patent is hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
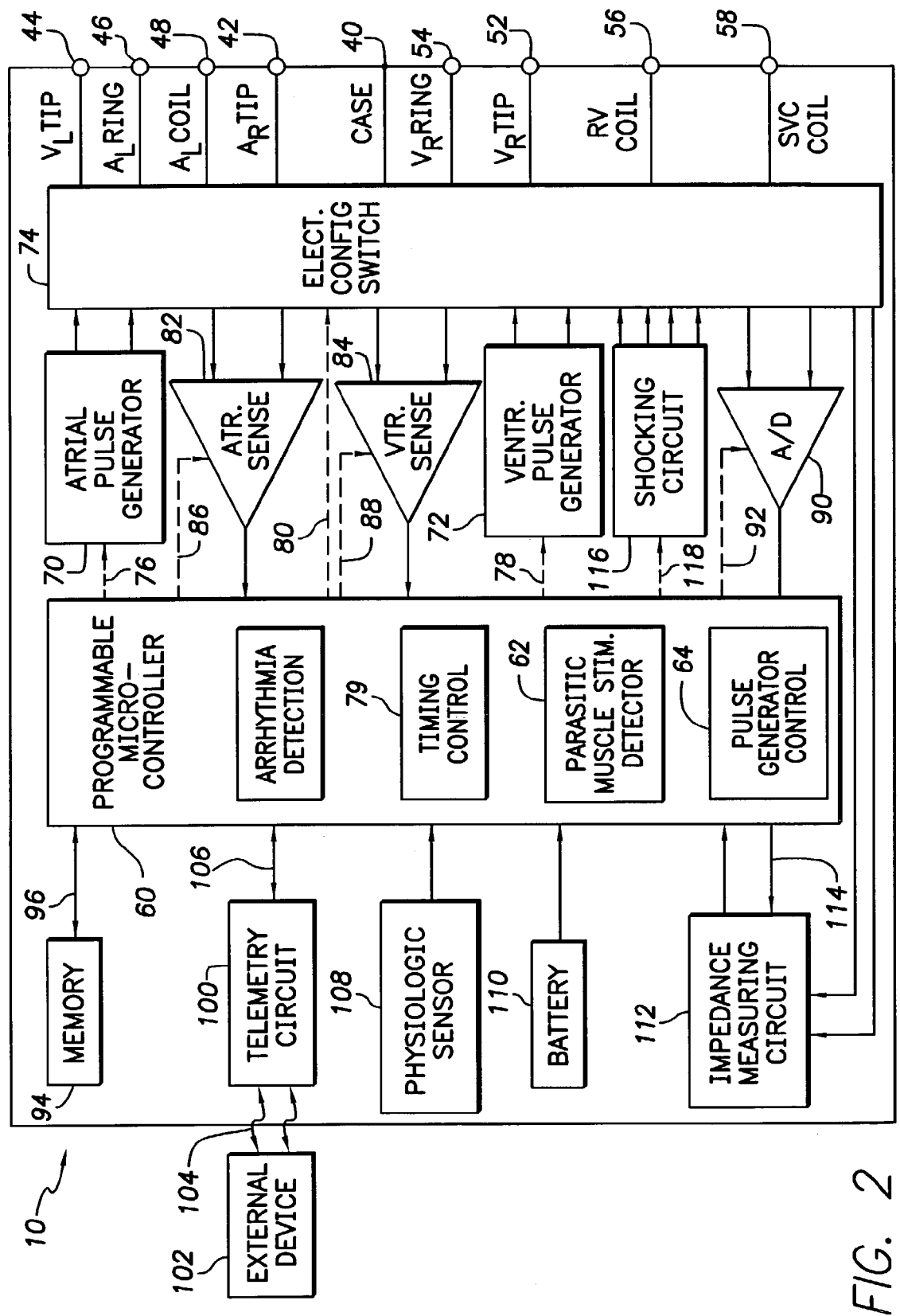
FIG. 2 is a functional block diagram of the device of FIG. 1 illustrating the basic elements thereof to provide cardioversion, defibrillation and pacing stimulation in all four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries.

As further shown in FIG. 2, the device 10 is shown as having an impedance measuring circuit 112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the device 10 has been generally described, the following description of the device 10 will now be directed to those elements and features which are more particularly related to the present invention. As previously described, the present invention enables stimulation of parasitic muscle tissue to be minimized which may otherwise result from the pacing of the heart. While the present invention is particularly directed to left heart side pacing where pacing thresholds are generally elevated, the present invention may also pertain to right heart side pacing as well as would be appreciated by those skilled in the art. Hence, the present invention may be employed for any one or all of right ventricular, right atrial, left atrial, and left ventricular pacing. For illustrative purposes only, the embodiment described herein will be directed to left ventricular pacing, and more particularly to unipolar left ventricular pacing wherein pacing pulses are applied to the left ventricular by a pacing electrode configuration including the left ventricular tip electrode 26 and the case 40.

In accordance with this embodiment of the present invention, the parasitic muscle stimulation is minimized by varying parameters of the left ventricular pacing pulses. These parameters include pulse amplitude (voltage or current) and pulse duration. The manner in which these parameters may be adjusted will be described subsequently.

Before the pacing pulse parameters are adjusted, it is first preferable to determine the pacing threshold at a predetermined pacing pulse duration. Once this is completed, it is then determined if the pacing pulses indeed cause parasitic muscle stimulation. If they do, then the pacing pulse parameters are adjusted, such as in the manner to be described subsequently, to minimize the parasitic muscle stimulation.

The pacing threshold may be determined by the microcontroller executing a suitable algorithm and through evoked response detection. To this end, the data acquisition system 90 may be coupled to the microcontroller, or other detection circuitry, for detecting an evoked response from the heart 12 in response to an applied pacing pulse, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a pacing pulse, the presence of which indicates that capture has occurred. The microcontroller 60 enables capture detection by triggering the appropriate pulse generator 70, 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. A capture threshold search would begin with a pulse amplitude at a desired starting point (either a high energy level or the level at which capture is currently occurring) and decreased with a constant pulse duration until capture is lost. The pulse amplitude may then be increased. The pulse amplitude at which capture is regained is known as the capture threshold. Thereafter, a safety margin is added to the capture threshold. The implementation of capture detection circuitry and algorithms are well known.

In the preferred embodiment, the stimulation device 10 further includes a physiologic sensor 108, commonly used in "rate-responsive" pacing wherein pacing rate is adjusted according to the exercise state of the patient. However, in accordance with this embodiment, the physiological sensor 108 may further be used to sense parasitic muscle tissue stimulation by generating an activity signal during pacing. A representative activity signal will be described subsequently. The physiologic sensor 108 is preferably an accelerometer of the type well known in the art.

As will be noted in FIG. 2, the device 10 further includes a parasitic muscle stimulation detector 62. In accordance with this embodiment, the microcontroller 60 processes the data from the physiologic sensor activity sensor to determine if the pacing pulses are causing parasitic muscle stimulation. If such stimulation is detected, a pulse generator control 64 is then initialized to adjust the pacing pulse parameters to enable the pacing pulses to capture the appropriate chamber of the heart while avoiding stimulation of parasitic muscle tissue.

Figure 3:
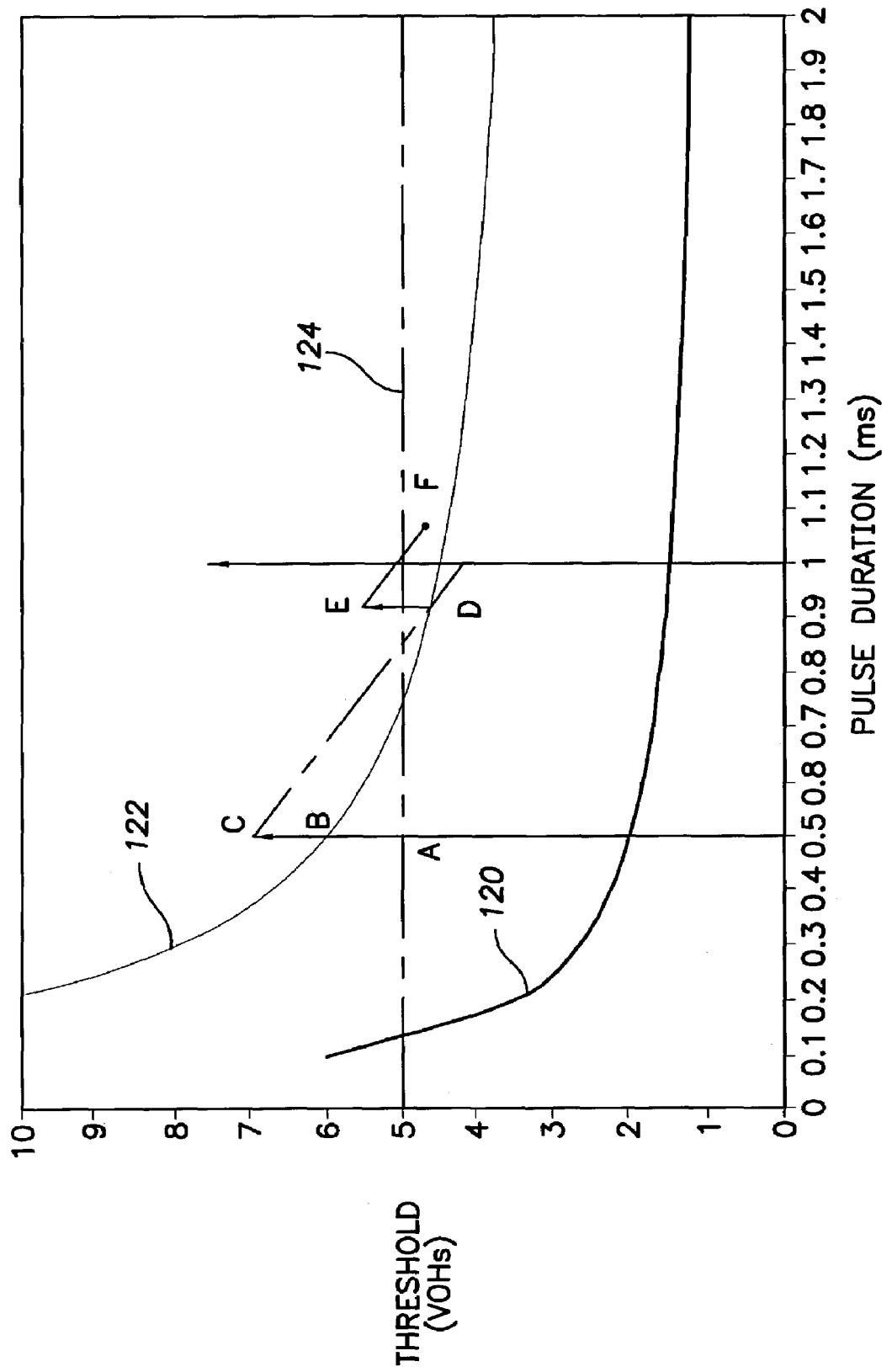
FIG. 3 is a graph illustrating the manner in which both low thresholds and high thresholds vary with output pulse width and a progression of output settings in accordance with an embodiment of the present invention.

FIG. 3 shows two curves 120 and 122 of pacing threshold (voltage required for capture) versus pacing pulse duration. The first curve 120 represents a typical threshold versus pulse duration relationship for a low threshold voltage environment such as in right ventricular pacing. It will be noted that the required pacing voltage amplitude decreases with increased pulse duration. However, at a pulse duration of about 0.5 ms, the pacing energy minimum occurs. This pulse duration is generally selected because it provides the minimum pacing energy and hence preserves battery power. As a result, threshold determinations are generally carried out with this fixed pulse duration. Curve 120 therefore indicates that a pulse amplitude above about 2 volts, with a duration of 0.5 ms, will capture the heart chamber. Generally a safety margin of about 0.25 volts is added to the determined threshold voltage, as is known in the art.

Also shown in FIG. 3 is the parasitic muscle stimulation threshold curve 124. It will be noted that the curve 124 is a straight line illustrating a constant stimulation threshold regardless of pulse duration. (Curve 124 actually curves up at the extreme left of the graph but is shown flat here for simplicity and since it is not relevant to this analysis.) It will also be noted that the pacing threshold of curve 120, at 0.5 ms, is well below the parasitic muscle stimulation threshold. Hence, pacing this heart chamber at the required capture amplitude with a duration of 0.5 ms will not cause parasitic muscle stimulation.

Curve 122, which may represent the required capture pulse voltage versus pulse duration for left ventricular unipolar pacing, is a different matter. Here it will be seen that the pulse voltage required to capture the left ventricle with a pacing pulse of 0.5 ms duration (point B) is greater than the parasitic muscle stimulation threshold (point A). Once a safety margin is added to the required capture pulse voltage amplitude, a greater yet pacing voltage results (point C).

In accordance with the present invention, once the pacing pulse amplitude voltage required to capture the given chamber is determined for a given pulse duration, the heart chamber is paced to determine if parasitic muscle tissue stimulation results from the pacing stimulation. If parasitic muscle tissue stimulation results, in accordance with the present invention, the pacing pulse parameters are adjusted so that the pacing pulses are enabled to capture the chamber on the heart while being unable to cause parasitic muscle tissue stimulation.

In accordance with this embodiment of the present invention, and as illustrated in FIG. 3, the pulse generator control 64 (FIG. 2) first adjusts the pacing pulse parameters by lengthening the pacing pulse widths and decreasing the pacing pulse amplitudes until the pacing pulses consistently stop stimulating parasitic muscle tissue. This corresponds to point D in FIG. 3. Unfortunately, at this point, the pacing output is just on the capture curve and hence does not provide reliable capture. Therefore, the pulse generator control 64 increases the pacing pulse amplitudes while maintaining the pacing pulse widths substantially constant until the pacing pulses both capture the chamber and stimulate parasitic muscle tissue. This is illustrated as point E in FIG. 3. Thereafter, the pulse generator control 64 once again lengthens the pacing pulse widths while decreasing the pacing pulse amplitude voltages until a pacing pulse captures the chamber and fails to stimulate parasitic muscle tissue. This corresponds to point F in FIG. 3. In transitioning from point E to point F in FIG. 3, the pulse generator control 64 decreases the incremental adjustments in the pulse widths and voltage amplitude to arrive at point F. However, these increments may be too large and result in an overshoot to a pacing voltage amplitude and duration which both fails to capture the heart chamber and stimulate parasitic muscle tissue. In this event, the adjustment steps of increasing the pacing pulse amplitude while maintaining the pacing pulse widths substantially constant until the pacing pulses both capture the chamber and stimulate parasitic muscle tissue, and then lengthening the pacing pulse widths while decreasing the pacing pulse amplitudes until a pacing pulse captures the chamber and fails to stimulate parasitic muscle tissue may be repeated but with decreased incremental changes in the pacing parameters. When overshoot is avoided, the last pacing voltage amplitude and duration may then be utilized for pacing the heart chamber. To the pacing pulse voltage amplitude, a safety margin may be added. However, if the added safety margin causes parasitic muscle tissue stimulation, further lengthening of the pacing pulse widths and decreasing of the pacing pulse amplitude voltages may be necessary.

Figure 4:
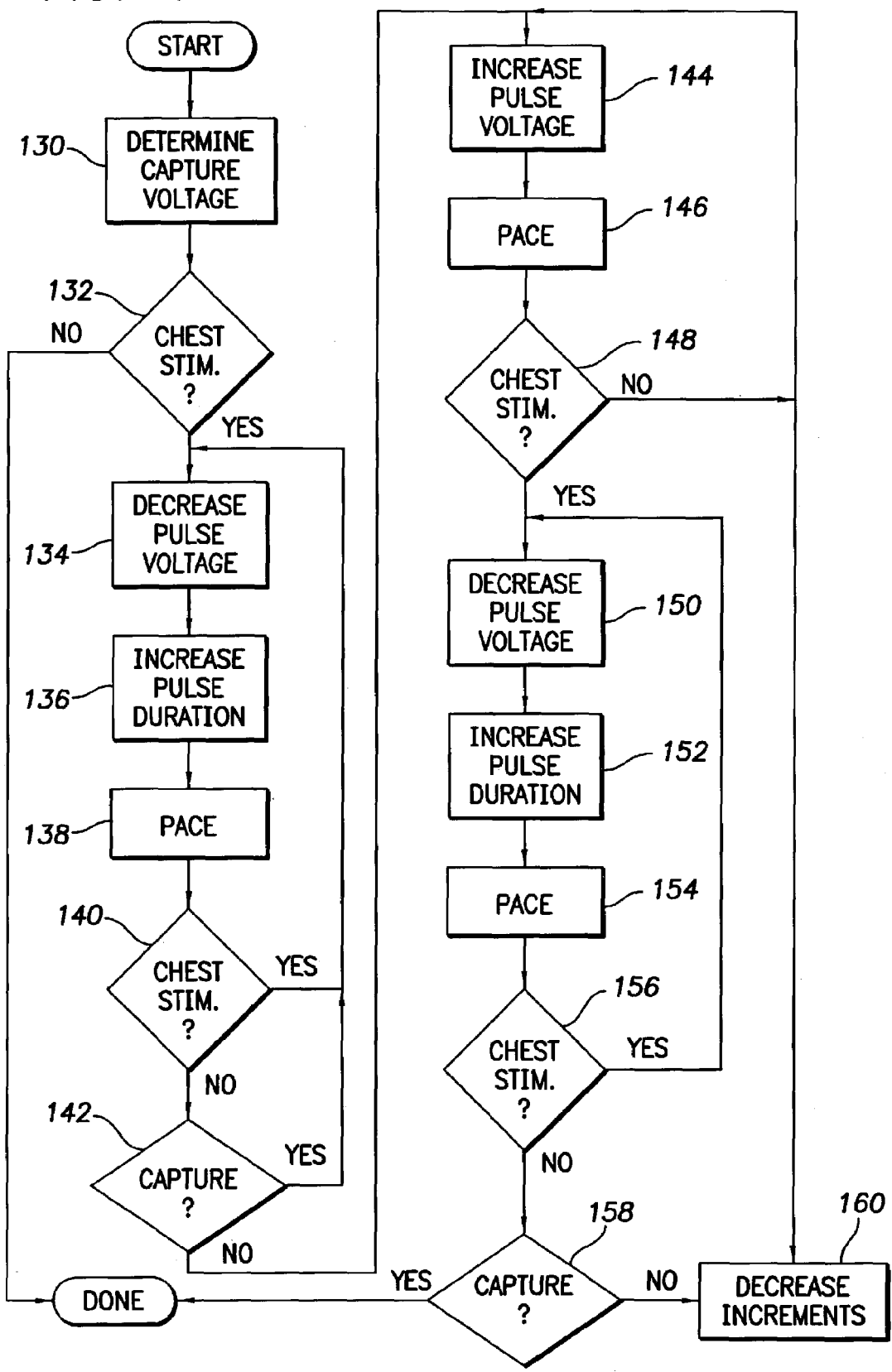
FIG. 4 is a flow chart describing an overview of the operation of one embodiment of the present invention.

In FIG. 4, a flow chart is shown describing an overview of the operation and novel features implemented in one embodiment of the device 10. In this flow chart, and the flow chart of FIG. 9 described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The process of FIG. 4 initiates with an activity block 130. Here, an initial capture voltage determination is made as, for example, in a manner as previously described. Once the initial capture voltage determination is made, the process advances to decision block 132 wherein the parasitic muscle stimulation detector 62 determines if there is parasitic muscle stimulation resulting from the last pacing pulse applied to the heart during the implementation of activity block 130. Here, it will be noted that the parasitic muscle stimulation has been abbreviated with the term "CHEST STIM". If the parasitic muscle stimulation detector 62 determines that there has been no parasitic muscle tissue stimulation, the process completes in as much as pacing the heart with pacing pulses having an amplitude and width as determined in activity block 130 will capture the heart while avoiding stimulation of parasitic muscle tissue and hence negating the need for pacing pulse adjustment. However, if parasitic muscle stimulation is detected in accordance with decision block 132, the process then advances to serial activity blocks 134 and 136 to be implemented by the pulse generator control 64. In activity block 134, the pulse generator control 64 decreases the pacing pulse voltage amplitude and in activity block 136 the pulse generator control 64 increases the pacing pulse duration. Once activity blocks 134 and 136 are completed, the process advances to activity block 138 wherein the heart chamber is paced with a pacing pulse having the decreased pulse amplitude and increased pulse duration. Once the heart chamber is paced, the process then advances to decision block 140 wherein it is once again determined if there has been parasitic muscle stimulation. If there has, the process returns to activity block 134 for a further decrement in pacing pulse amplitude and increment in pacing pulse duration. If there has been no parasitic muscle stimulation detected, the process then advances to decision block 142 wherein it is determined if the pacing pulse captured the heart chamber. If it did, the process returns to activity block 134. If it did not capture the chamber, the process advances to activity block 144 wherein the pacing pulse voltage amplitude is increased. Once the pacing pulse voltage amplitude is increased, the process advances to activity block 146 wherein the pacing pulse is applied to the chamber of the heart. After the pacing pulse is applied in accordance with activity block 146, the process advances to decision block 148 wherein it is determined if there has been parasitic muscle stimulation. If there hasn't, the process returns to activity block 144. Activity blocks 144 and 146 are repeated until a pacing pulse results in parasitic muscle stimulation. When this occurs as determined in decision block 148, the process advances to activity block 150 wherein the pacing pulse voltage amplitude is decreased and then to activity block 152 wherein the pacing pulse width is increased. Following activity block 152, the pacing pulse is applied to the chamber of the heart in accordance with activity block 154. After the pacing pulse is applied in activity block 154, the process advances to decision block 156 to determine if the last applied pacing pulse resulted in parasitic muscle stimulation. If it did, the process returns to activity block 150. If it did not, the process advances to decision block 158 wherein it is determined if the last applied pacing pulse captured the chamber of the heart. If it did, the process completes because a pacing pulse amplitude voltage and duration has been determined which will capture the chamber of the heart but not result in parasitic muscle stimulation.

However, if it is determined in decision block 158 that the last applied pacing pulse failed to capture the heart chamber, the process has over shot its mark. In other words, the last applied pacing pulse not only failed to stimulation parasitic muscle tissue, but it also failed to capture the heart. As a result, the process advances to activity block 160 wherein the increments in decreasing the pacing pulse amplitude voltage and increasing the pacing pulse widths are decreased and the process returns to activity block 144. The process is now repeated from activity block 144 through decision block 158 using the decreased increments.

The process of FIG. 4 results in a pacing pulse having an amplitude voltage and duration which captures the chamber of the heart and avoids stimulating parasitic muscle tissue. A further step may be added to the flow chart of FIG. 4 wherein a safety margin of, for example, 0.25 volts may be added to the determined pulse amplitude voltage. Should such a safety margin result in parasitic muscle stimulation, the process of FIG. 4 may be repeated.

Figure 5:
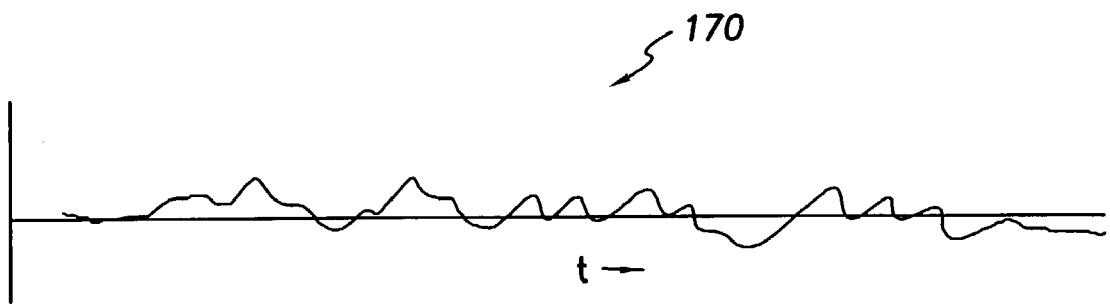
FIG. 5 is a plot illustrating an activity signal of ambient patient activity over time.

Referring now to FIG. 5, it illustrates an ambient activity signal 170 illustrative of the type of activity signal provided by the physiologic sensor 108. It will be noted that the ambient activity signal 170 has relatively minor variations or fluctuations due to the fact that the patients requiring left heart side pacing generally are relatively inactive.

Figure 6:
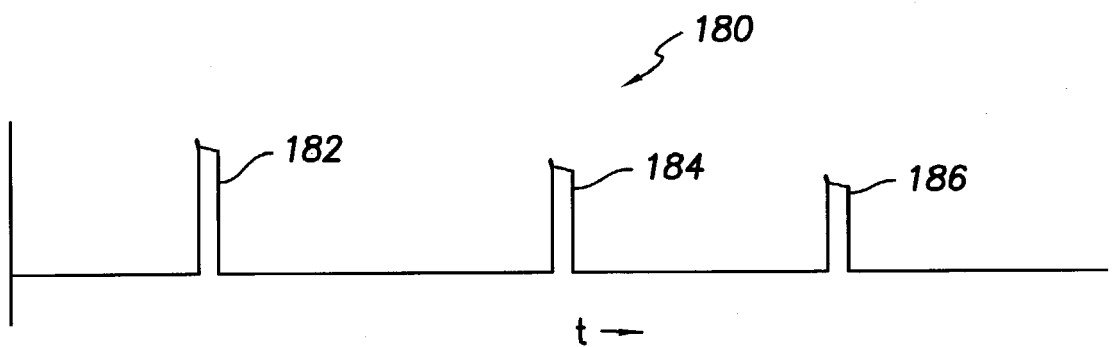
FIG. 6 is a plot of applied pacing pulses.

FIG. 6 illustrates a pulse train 180 of pacing pulses 182, 184, and 186. For purposes of this description, it is assumed that the pacing pulses have pacing voltage amplitudes and durations to cause parasitic muscle tissue stimulation.

Figure 7:
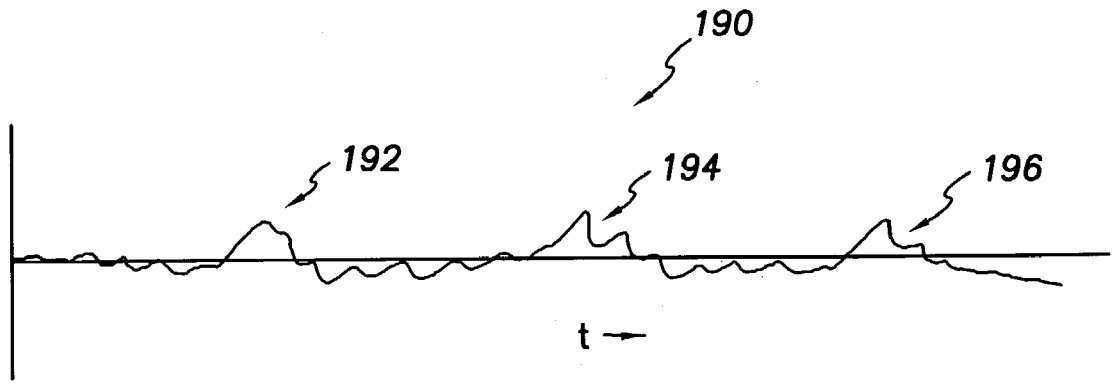
FIG. 7 is a plot illustrating an activity signal of patient activity resulting from the pacing pulses of FIG. 6.

FIG. 7 shows an activity signal 190 similar to the activity signal 170 of FIG. 5 except for elevated activity portions 192, 194, and 196. It will be noted that the elevated activity portions 192, 194, and 196 correspond to pacing pulses 182, 184, and 186. Hence, the elevated activity portions 192, 194, and 196 are indicative of parasitic muscle stimulation. The occurrence of the elevated activity portions 192, 194, and 196 may be utilized to advantage in detecting parasitic muscle tissue stimulation.

Figure 8:
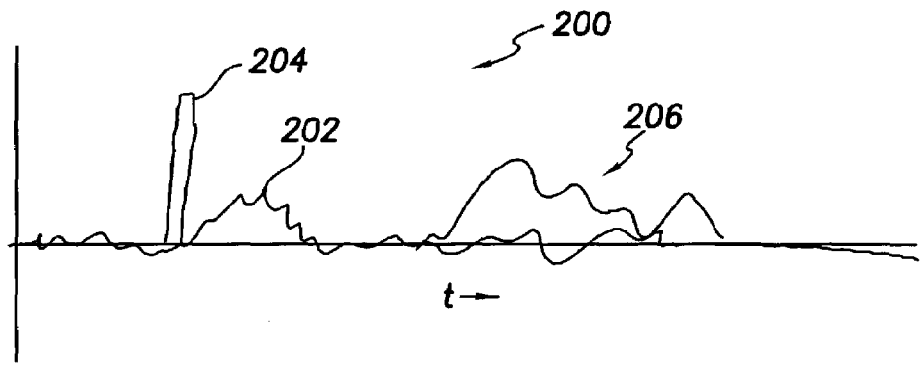
FIG. 8 is a plot of an averaged activity signal.

More particularly, since the elevated activity portions 192, 194, and 196 occur immediately after the application of pacing pulses 182, 184, and 186, respectively, the parasitic muscle tissue stimulation detection may be enhanced by synchronizing the detection or processing of the activity signal synchronized to the application of the pacing pulses. FIG. 8 illustrates a waveform 200 which results when the elevated activity portions are averaged over a plurality of cardiac cycles. Here, the elevated activity portion average 202 is clearly noted in relation to an averaged overlaid pacing pulse 204. Following the elevated activity portion average 202 are the cardiac components 206 resulting from the pacing pulses. As a result, the data provided immediately after each pacing pulse may be processed and averaged to provide a substantially increased signal-to-noise ratio in determining the occurrence of parasitic muscle stimulation. The foregoing may be utilized to advantage in the process illustrated in FIG. 9.

Figure 9:
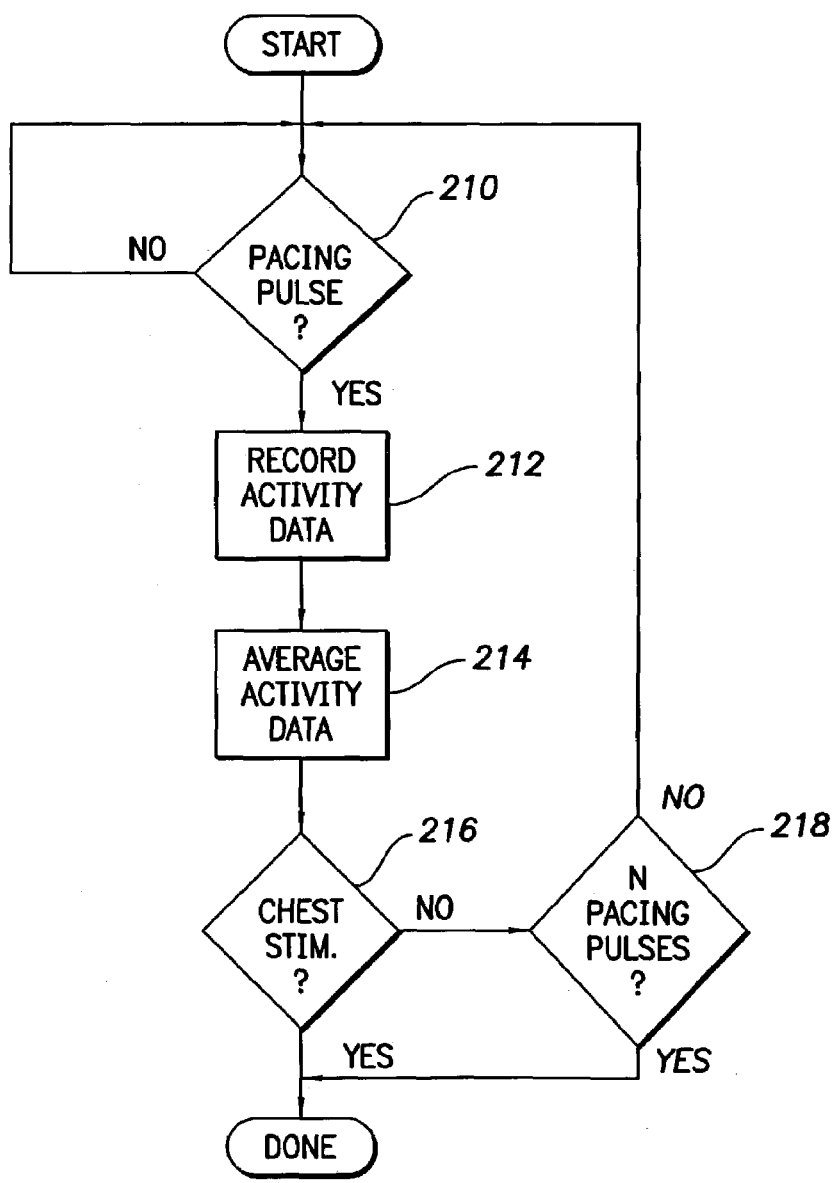
FIG. 9 is a flow chart describing the operation of detecting parasitic muscle tissue stimulation in accordance with an embodiment of the present invention.

The flowchart of FIG. 9 initiates with decision block 210 wherein it is determined if a pacing pulse has been applied. If a pacing pulse has not been applied, the process returns. However, when a pacing pulse is applied, the process advances to activity block 212 wherein the activity data from the activity signal is recorded. This corresponds to the data occurring during a window which would encompass the elevated activity portion, such as elevated activity portion 192 (FIG. 7) immediately following pacing pulse 182 (FIG. 6). After the data is recorded in activity block 212, the process then advances to activity block 214 wherein the recorded activity data is averaged. Obviously, if only one pacing pulse has been applied, the data resulting from activity block 214 will be identical to the data resulting from activity block 212.

Following activity block 214, it is determined if there has been parasitic muscle stimulation in decision block 216 based upon the peak amplitude of the averaged data. As a result, if the peak of the averaged elevated activity portions is of sufficient amplitude to be considered parasitic muscle stimulation, the process completes. In completing, this may permit, for example, the pulse generator control 64 (FIG. 2) to adjust the pacing pulse parameters to avoid the parasitic muscle stimulation. However, if in decision block 216, the averaged peak is not sufficient to substantiate parasitic muscle stimulation, the process advances to decision block 218 wherein it is determined if there have been a required number (N) of pacing pulses. If there have not, the process returns to decision block 210. If there has, the process completes since a preset number (N) of pacing pulses failed to result in the detection of parasitic muscle stimulation.

While the invention has been described by means of specific embodiments and applications thereof, it is understood that numerous modifications and variations may be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
   a sensor that is operative to sense a parameter associated with parasitic muscle tissue stimulation;
   a pulse generator adapted to provide pacing pulses to a chamber of a heart; and
   a control circuit coupled to the sensor and to the pulse generator, and that is operative to adjust one or more parameters of the pacing pulses to control the degree of parasitic muscle tissue stimulation;

wherein the one or more parameters of the pacing pulses comprise at least one of pulse width and pulse amplitude and wherein the control circuit is operative to lengthen the pacing pulse width and decrease the pacing pulse amplitude; and wherein the control circuit lengthens the pacing pulse width until a capture threshold amplitude is below a parasitic muscle tissue stimulation threshold.

2. The device of claim 1 wherein the control circuit sets the pacing pulse amplitude to an amplitude above a capture threshold and below the parasitic muscle tissue stimulation threshold.

3. The device of claim 2 wherein the control circuit sets the pacing pulse amplitude to an amplitude above the pacing threshold at a given pacing pulse width prior to increasing the pacing pulse widths.

4. An implantable cardiac stimulation device comprising:
a sensor that is operative to sense a parameter associated with parasitic muscle tissue stimulation;
a pulse generator adapted to provide pacing pulses to a chamber of a heart; and
a control circuit coupled to the sensor and to the pulse generator, and that is operative to adjust one or more parameters of the pacing pulses to control the degree of parasitic muscle tissue stimulation;
wherein the one or more parameters of the pacing pulses comprise at least one of pulse width and pulse amplitude and wherein the control circuit is operative to lengthen the pacing pulse width and decrease the pacing pulse amplitude; and
wherein the control circuit further comprises a pulse generator control to lengthen the pacing pulse width and to decrease the pacing pulse amplitude until the pacing pulses fail to both capture the chamber and stimulate parasitic muscle tissue, then to increase the pacing pulse amplitude while maintaining the pacing pulse widths substantially constant until the pacing pulses both capture the chamber and stimulate parasitic muscle tissue, and then to lengthen the pacing pulse width while decreasing the pacing pulse amplitude until a pacing pulse captures the chamber and fails to stimulate parasitic muscle tissue.

5. An implantable cardiac stimulation device comprising:
a sensor that is operative to sense a parameter associated with parasitic muscle tissue stimulation;
a pulse generator adapted to provide pacing pulses to a chamber of a heart;
a control circuit coupled to the sensor and to the pulse generator, and that is operative to adjust one or more parameters of the pacing pulses to control the degree of parasitic muscle tissue stimulation; and
a lead system adapted to be coupled to the pulse generator and having at least one electrode that provides the pacing pulses to a left ventricle.

6. An implantable cardiac stimulation device comprising:
means for detecting parasitic muscle tissue stimulation;
pulse generator means for providing pacing pulses to a chamber of a heart of a patient; and
control means for adjusting one or more parameters of the pacing pulses to control the degree of parasitic muscle tissue stimulation;
wherein the control means comprises means for lengthening the pacing pulse width until a capture threshold amplitude is below a parasitic muscle tissue stimulation threshold.

7. The device of claim 6 wherein the control means comprises means for setting the pacing pulse amplitude to an amplitude above the capture threshold amplitude and below the parasitic muscle tissue stimulation threshold.

8. The device of claim 6 wherein the control means comprises means for setting the pacing pulse amplitude to an amplitude above the capture threshold at a given pacing pulse width prior to increasing the pacing pulse widths.

9. An implantable cardiac stimulation device comprising:
means for detecting parasitic muscle tissue stimulation;
pulse generator means for providing pacing pulses to a chamber of a heart of a patient;
control means for adjusting one or more parameters of the pacing pulses to control the degree of parasitic muscle tissue stimulation; and
lead means adapted to be coupled to the pulse generator and providing the pacing pulses to a left ventricle.

10. The device of claim 9 wherein the one or more parameters of the pacing pulses include pulse width and pulse amplitude and wherein the control means includes means for lengthening the pacing pulse width and decreasing the pacing pulse amplitude.

11. In an implantable cardiac stimulation device, a method comprising:
applying pacing pulses to a chamber of a heart of a patient;
detecting parasitic muscle tissue stimulation in response to the pacing pulses; and
adjusting one or more parameters of the pacing pulses to control the degree of parasitic muscle tissue stimulation;
wherein the one or more parameters of the pacing pulses comprise at least one of pulse width and pulse amplitude, and wherein adjusting one or more parameters comprises lengthening the pacing pulse width and decreasing the pacing pulse amplitude.

12. The method of claim 11 wherein lengthening the pacing pulse width comprises lengthening the pacing pulse width until a capture threshold is below a parasitic muscle tissue stimulation threshold.

13. The method of claim 12 wherein adjusting comprises setting the pacing pulse amplitude to an amplitude above the capture threshold and below the parasitic muscle tissue stimulation threshold.

14. A cardiac stimulation device comprising:
a pulse generator that applies stimulation pulses to a chamber of a heart of a patient;
a sensor that senses parasitic muscle activity of the patient following one of the stimulation pulses, and that provides a corresponding activity signal; and
a parasitic muscle tissue stimulation detector that processes the activity signal and detects parasitic muscle tissue stimulation resulting from the stimulation pulses.

15. The device of claim 14 wherein the sensor comprises an accelerometer.

16. In a cardiac stimulation device, a method comprising:
applying stimulation pulses to a chamber of a heart;
sensing parasitic muscle activity of the patient following at least one of the stimulation pulses, and providing a corresponding activity signal; and
detecting parasitic muscle tissue stimulation resulting from the stimulation pulses based on the activity signal.

* * * * *